United States Patent [19]

Ansari et al.

[11] 4,100,110
[45] Jul. 11, 1978

[54] ISOLONGIFOLENE PRINS REACTION COMPOUNDS IN PERFUMERY

[75] Inventors: Hifzur Rahman Ansari, Rayleigh; Neville Unwin, Surbiton; Horst Richard Wagner, Woodford Green, all of England

[73] Assignee: Bush Boake Allen Limited, London, England

[21] Appl. No.: 603,908

[22] Filed: Aug. 11, 1975

[30] Foreign Application Priority Data

Aug. 9, 1974 [GB] United Kingdom ............... 25244/74

[51] Int. Cl.$^2$ .............................................. C11B 9/00
[52] U.S. Cl. ................... 252/522; 560/249; 560/238; 560/233; 260/586 C; 260/586 F; 260/586 G; 252/132; 424/76; 260/598; 568/819; 568/817
[58] Field of Search ................ 252/522; 260/586, 489, 260/617 F, 598, 494, 631.5

[56] References Cited

U.S. PATENT DOCUMENTS

| | | | |
|---|---|---|---|
| 3,647,847 | 3/1972 | Curtis et al. | 260/489 |
| 3,718,698 | 2/1973 | Hall | 260/587 |
| 3,745,131 | 7/1973 | Curtis et al. | 252/522 |

*Primary Examiner*—Veronica O'Keefe
*Attorney, Agent, or Firm*—Flynn & Frishauf

[57] ABSTRACT

Novel compounds of use in perfumery are obtained by performing a Prins reaction on isolongifolene. They include novel primary and secondary alcohols, their esters and the corresponding aldehydes and ketones.

24 Claims, No Drawings

ISOLONGIFOLENE PRINS REACTION COMPOUNDS IN PERFUMERY

The present invention relates to novel sesquiterpene products which are of use in perfumery, to their preparation and to certain novel compounds which may be isolated from the products. The invention also relates to perfumery compositions of the type where a number of odoriferous ingredients of synthetic or natural origin are admixed or compounded to form a perfumery concentrate. Such concentrates may find use as such or after dilution but more usually they are added in small proportions to other materials such as to space sprays or to soap, detergent, cosmetic or deodorant compositions or to substrates such as fabrics, fibres or paper products in order to provide them with agreeable olfactory properties. Thus, such concentrates are products of commerce and the perfumery concentrates may comprise a simple or complex mixture of individual perfumery compounds.

It is known that many terpene compounds have characteristic odours, and that some are particularly suitable for use in perfumery. It has never, however, been possible to draw a complete correlation between structure and odour, and one cannot therefore generally predict which compounds will possess a useful or pleasing odour, or what the particular odour description of any given compound will be.

One useful starting material for the synthesis of perfumery ingredients is the sesquiterpene longifolene, and a number of valuable odoriferous terpene compounds have been sythesised in one or more stages commencing from longifolene. A known first stage in some of these syntheses is the conversion of longifolene to isolongifolene (I).

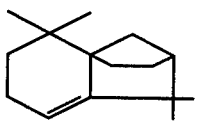
(I)

However, many derivatives of isolongifolene are not useful in perfumery.

We have now discovered a novel class of products which may be prepared from iso-longifolene which we have found to possess particularly desirable perfumery properties.

Our novel products are obtained from iso-longifolene by means of a Prins reaction followed optionally by a reduction or saponification. We have isolated from our novel products certain novel compounds of particular value in perfumery. The Prins reaction involves the reaction of an aldehyde with an olefin, preferably in the presence as catalyst of a Lewis acid or mineral acid. The reaction may be carried out:

(a) Using formaldehyde in a carboxylic acid as solvent to convert an olefin to an ester $R''$-$CH_2OR$ (where R is an acyl residue of the carboxylic acid solvent.

(b) Using a formaldehyde condensate such as paraformaldehyde in an autoclave, to provide a primary alcohol $R''CH_2OH$ or (c) Using a higher aldehyde to provide a secondary alcohol

Under certain conditions, this reaction may alternatively or additionally provide the ketone

Usually the original olefin undergoes total or partial rearrangement during the course of the reaction, resulting in the formation of products in which the olefinic bond has shifted to an adjacent position. Thus the olefin $CH_3$—$CH$=$CH_2$ will provide products in which $R''$ is $CH_2$=$CH$—$CH_2$—. However, in particular instances the olefinic bond may be unable to shift to the 2,3 position for structural reasons. In such circumstances the olefin

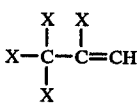

may provide products in which $R''$ is

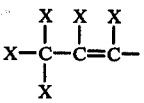

Alternatively, the compound may undergo structural rearrangement, e.g. cyclisation with consequent removal of the olefinic bond.

The aforesaid esters prepared by method (a) may also be saponified to provde the corresponding primary alcohols similar to those obtained by method (b). The aforesaid alcohols prepared by method (c) may be oxidised using, for example, chromic acid to provide the corresponding ketones. The primary alcohols prepared according to method (b) or by saponification of the product of method (a) may be oxidised to the corresponding aldehydes using oxidising agents conventionally employed for the conversion of primary alcohols to aldehydes.

The aforesaid aldehydes may be reacted with alkyl magnesium iodides to form secondary alcohols corresponding to those obtained by method (c). These may be oxidised to ketones as previously described.

The secondary alcohols having the structure which is obtained by method (c) may be esterified using any conventional esterification method.

All the aforesaid Prins reaction products in which the olefinic bond has been retained may also be catalytically hydrogenated to provide the corresponding saturated compounds.

Generally, therefore, our invention provides a method for the preparation of perfumery products which comprises reacting iso-longifolene with an aldehyde having from 1 to 6 carbon atoms in the presence of a catalytic amount of a Prins reaction catalyst.

According to a first particular embodiment, the invention provides a method which comprises reacting iso longifolene with formaldehyde and sufficient formic acid to dissolve the mixture.

According to a second particular embodiment the invention provides a method which comprises reacting iso-longifolene with formaldehyde in the presence of a carboxylic acid having from 1 to 6 carbon atoms and a catalytic quantity of a Lewis acid or strong mineral acid to form an ester and, optionally, thereafter saponifying the product with hot aqueous alkali, to form primary alcohol.

According to a third particular embodiment the invention provides a method which comprises reacting iso-longifolene with a formaldehyde condensate in an autoclave at a temperature above the normal pressure boiling point of the mixture to provide primary alcohols.

According to a fourth particular embodiment any of the aforesaid primary alcohols are subsequently oxidised to the corresponding aldehydes.

According to a fifth particular embodiment the aldehydes prepared according to the fourth particular embodiment are reacted with an alkyl magnesium iodide having from 1 to 5 carbon atoms to form a secondary alcohol.

According to a sixth particular embodiment the secondary alcohol prepared according to the fifth particular embodiment may be oxidised to a ketone.

According to a seventh particular embodiment iso-longifolene is reacted with an aldehyde having from two to six carbon atoms in the presence of a catalytic amount of a Prins reaction catalyst to form secondary alcohols followed, optionally, by oxidation of the alcohols to ketones The secondary alcohols may optionally be esterified.

According to an eighth particular embodiment any of the aforesaid embodiments is followed by the step of reacting the product with hydrogen in the presence of a hydrogenation catalyst to form a saturated product.

According to a second general embodiment our invention provides as novel perfumery ingredients the volatile products of a Prins reaction as hereinbefore described on iso-longifolene, followed, optionally by saponification, reduction, oxidation or hydrogenation as hereinbefore described. Our invention further provides perfumery compositions comprising the aforesaid products of the invention.

According to a further embodiment the invention provides novel perfumery compounds which may be isolated from the aforesaid products of the invention and which have the formula XYR, wherein X is (II), (III) or (IV)

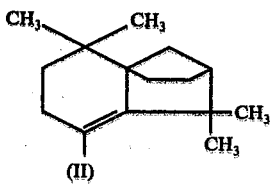
(II)

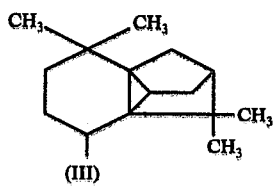
(III)

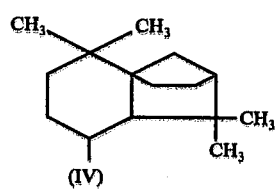
(IV)

Y is $$-\overset{O}{\underset{}{C}}- \text{ or } -\overset{OR'}{\underset{}{CH}}-,$$

R is H or an alkyl group having from 1 to 5 carbon atoms and R' is H or an acyl residue containing 1 to 6 carbon atoms.

The Prins reaction is preferably carried out with formaldehyde in sufficient carboxylic acid having from 1 to 6 carbon atoms to function as a solvent. The carboxylic acid, may, preferably, be formic acid or acetic acid. The carboxylic acid may alternatively be for example, propionic acid, butyric acid, iso-butyric acid, valeric acid or caproic acid. The carboxylic acid forms the esters X — CH$_2$OR' where R' is the acyl residue of the carboxylic acid. If a primary alcohol is desired the carboxylic acid may be omitted.

Formic acid is capable of catalysing the reaction sufficiently on its own, without the need for any additional catalyst, but if higher carboxylic acids are employed, and preferably also when formic acid is used there is additionally present an acid catalyst. The catalyst may be any of those normally employed in Prins reactions. For example it may be a lewis acid such as BF$_3$ or its etherate, ZnCl$_2$ or SnCl$_4$. Alternatively, it may be a mineral acid such as H$_2$SO$_4$, H$_3$PO$_4$ or HCl, although the last is not preferred due to the risk of forming carcinogenic by-products.

The catalyst may generally be present in the amounts hitherto conventional for Prins reactions. For example from 0.5 to 10%, preferably 1 to 5% e.g. 1 to 2% of the catalyst, based on the weight of the reaction mixture may be used.

The reaction is preferably carried out below the refluxing temperature of the system, to avoid degradation. Although the reaction will occur at any temperature e.g. to boiling point, it is preferred to maintain the temperature between 60° C and 90° C. The reaction is usually maintained for from 1 to 24 hours, preferably 6 to 16 hours.

The relative proportions of formaldehyde and iso-longifolene are not critical. The reaction involves equimolar addition of formaldehyde to the terpene and approximately equimolar proportions may therefore be used.

However, an excess of either reagent is technically possible although in practice, since the iso-longifolene is, by far, the most expensive component of the mixture it is preferred to use a small excess of the formaldehyde, e.g. up to 20% of the stoichiometric amount. The carboxylic acid may be present in any desired proportion, depending on the proportion of esters required in the product. If a product consisting of alcohols is required the carboxylic acid may be omitted altogether. Increasing the proportion of carboxylic acid increases the proportion of ester in the product. Generally, it is preferred to employ the carboxylic acid as solvent and therefore the carboxylic acid is preferably present in a sufficient proportion to dissolve the other components of the reaction mixture.

It is possible, but usually not preferred, to carry out the reaction in an inert solvent such as a hydrocarbon solvent in addition to or instead of the carboxylic acid. The reaction mixture may optionally be anhydrous.

The reaction may be carried out using an aliphatic aldehyde having from 2 to 5 carbon atoms in place of formaldehyde, under similar conditions to those hereinbefore described in relation to formaldehyde. It is also possible to carry out the reaction in an autoclave at, for example, 150° to 250° C under autogenous pressure.

The reaction product is preferably fractionally distilled to separate the effective perfumery product from unreacted iso-longifolene and a residue of degradation products.

The effective perfumery product has been found to consist of a mixture of compounds of the formula:

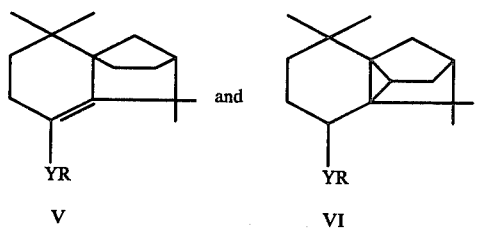

with a minor proportion of other $C_{16}$ isomers. It is possible to isolate these individual compounds by fractional distillation.

The proportion of (VI) to (V) in the product varies according to the duration of the reaction. For example, on longer treatment, especially in the presence of a strong acid catalyst, the initially formed (VI) can rearrange to (V). Short reaction times therefore, favour products containing a high proportion of (VI), longer reaction times favour products containing a high proportion of (V).

Where the reaction has been carried out under conditions adapted to provide an ester $XCH_2OR'$ the product may be saponified by means well known in the art for the saponification of carboxylic esters. (e.g. boiling with aqueous alkali such as sodium hydroxide) to provide the corresponding primary alcohol, $XCH_2OH$.

Primary alcohols $XCH_2OH$ prepared in accordance with the invention may be oxidised to aldehydes $XCHO$, by means well known in the art for the oxidation of primary alcohols to aldehydes. For example, they may be oxidised with chromic acid.

Alcohols

prepared according to the invention may be oxidised to the corresponding ketones

by means well known in the art for oxidising alcohols to ketones.

Any of the unsaturated compounds prepared according to the invention may be hydrogenated to the corresponding saturated compounds using hydrogen and a hydrogenation catalyst, examples of which are well known in the art, such as platinum or palladium.

Perfumery compounds and mixtures of compounds which may be distilled from reaction mixture may be incorporated in perfumery formulations and perfumed products. The products of the invention tend, generally to have a woody or amber character. In particular many of the products are distinctly reminiscent of cedar or vetiver and may be used in formulation of the type for which cedar, vetiver or amber are useful.

The novel perfumery compositions may be compounded according to recognised techniques of perfumery employing known odorifierous perfumery ingredients, e.g. techniques and ingredients mentioned in the standard text books "Soap Perfumery and Cosmetics" by W. A. Poucher, 7th Edition, published by Chapman & Hall (London) 1959; "Perfume and Flavour Chemicals" by S. Arctander, published by the author (Montclair) 1959 and "Perfume and Flavour Materials of Natural Origin" also by S. Arctander, self-published, Elizabeth N.J., 1960. The relevant disclosures of the aforesaid text books are hereby incorporated by reference herein. Specific odoriferous ingredients which may be blended with the compounds or products of this invention include the derivatives of 2,6 -dimethyl-2-alkoxy octan-7-ol (as claimed in our Dutch Patent Application No. 72.15238), vetivert oil, vetiverol, vetiveryl acetate, guaiac wood oil, guaiac wood acetate, coumarin musk ketone, lauric aldehyde, benzyl acetate, lemon oil, dimethyl benzyl carbinol, dimethyl benzyl carbinyl acetate, rose absolute, jasmin absolute, ionones, isononyl acetate, methyl phenyl acetate, styrallyl acetate, B phenyl ethanol, citronellol, citronellal, hydroxy citronellal, geranium oil, geraniol, linalol, nerol, lavandin oil, linalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdanum resin, methyl ionones, dihydromyrcenol, orange oil, vanillin, ethylvanillin, olibanum resin, musk ambrette, rhodinol, mandarin oil, methylnonyl acetaldehyde, neroli oil, cedrol, oakmoss, isovalanone, eugenol, iso-eugenol, cedarwood oil, p-tert-butyl cyclohexyl acetate.

Typically the compounds of our invention are blended with at least two, usually at least five and preferably at least ten of the foregoing ingredients.

It has been found that these compounds have a high degree of utility in perfumery compositions both in the capacity of odoriferous ingredients and fixatives. They can be usefully employed in a wide range of proportions; say from 0.01 to 20% by weight on the compounded perfumery compositions, In some cases it may be desired to use from 1 to 10 or 1 to 20 or 2 to 10% by weight on the said basis whilst in other cases from 5 to 20 e.g. 3 to 30% parts may be required The compounded perfumery compositions of the invention find use in a wide variety of perfumed materials. They may be usefully employed in toilet preparations, space sprays or can be blended in soap, toilet waters, face creams, talcum powder, baby lotions and sun cream preparations. They may also be used to perfume substrates such as fibres, fabrics and paper products.

The products of our invention are particularly effective when used in conjunction with essential oils such as those of cedarwood, sandalwood, vetiver, lavender, bergamot, geranium, patchouli, oakmoss or Clary sage, and/or with natural or synthetic materials such as Musk Ambrette Musk Ketone, Musk Xylene, Cedrol and Cedryl Acetate, Acetyl Cedrene, Vetiverol, and Vetiveryl Acetate, Methyl Ionone, Coumarin, Linalool, Linalyl Acetate, Geraniol, Citronellol, Phenyl Ethyl Alcohol, Benzyl Acetate, Eugenol, Isoeugenol, Amyl - and Hexylcinnamin Aldehyde, or Hydroxycitronellal.

The invention is illustrated by the following examples.

EXAMPLE 1

Isolongifolene (204 g. 1 mole) was treated with paraformaldehyde (36 g. 1.2 moles) in formic acid (138 g. 3 moles) at 90° C over a period of 16 hours. After this duration, about 75% of isolongifolene had been converted into a mixture of C-16 formates. The product was washed twice with water, dried and distilled mainly in two fractions, namely, the hydrocarbon fraction and the formate fraction as indicated by the boiling points given below:

| Fraction 1 | 75 g. | 70 – 100° C. 0.5 mm. mainly isolongifolene |
|---|---|---|
| Fraction 2 | 110 g. | 110 – 120° C. 0.5 mm. mainly C-16 formates |
| Residue | 35 g. | |

This represents w/w yield of about 84.5% based on consumed isolongifolene. The formate fraction comprised a mixture of

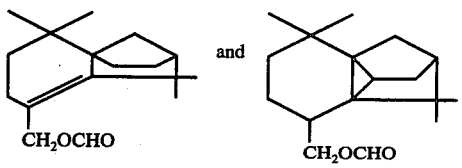

determined by N.M.R. and I.R. analysis, and had a pronounced cedarwood-vetiver odour of great tenacity, with amber, clary sage dryout.

EXAMPLE 2

Example 1 was repeated using 180 g. acetic acid and 2 g. sulphuric acid instead of the formic acid. The mixture was heated at 60° C. A similar yield of the corresponding acetate esters was obtained having a strong cedar-vetiver odour reminiscent of cedryl and vetiveryl acetates.

EXAMPLE 3

The mixtures of formates (265 g.) and acetates (276 g.), prepared according to examples 1 and 2 respectively, were each saponified by boiling with 30% aqueous sodium hydroxide (48 g.) over a period of 6 hrs. to give a mixture of corresponding alcohols. The product (230 g.) was distilled through a short column and in each case had a soft, woody odour, reminiscent of cedrol.

EXAMPLE 4

A mixture of alcohols (234 g.) prepared according to example 3 was dissolved in 250 c.c. of glacial acetic acid, and cooled in a water bath while sodium dichromate (170 g.) in 750 c.c. of acetic acid was added over a period of 2 hours. After this the reaction mixture was allowed to stand at ambient temperature for 20 hours. The mixture of aldehydes thus formed was isolated by work up with water and distilled to give the finished product (175 g.) with a strong cedar-vetiver odour and a pronounced amber note on dry-out.

EXAMPLE 5

An ethereal solution of the aldehyde mixture (232 g.) prepared according to example 4 was slowly added to methylmagnesium Iodide which was generated from methyl Iodide (142 g.) and magnesium (24.3 g.) in ether (500 c.c.). After the initial exothermic reaction had subsided, the reaction mixture was refluxed for further 2 hr. Work up with dilute ammonium chloride solution followed by distillation gave a mixture of alcohols (IX) and (X) in 93% yield.

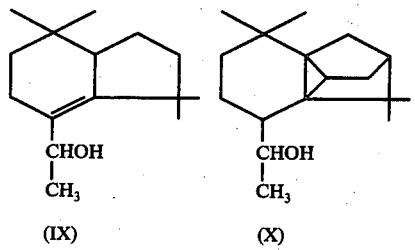

(IX)        (X)

Chromic acid oxidation of the above alcohols using the procedure described in example 4 gave the corresponding ketones (XI) and (XII) in almost quantitative yield. The ketone mixture had a strong woody-orris odour with ambery undertones.

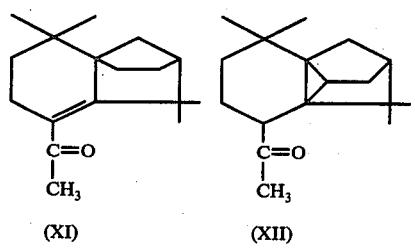

(XI)        (XII)

EXAMPLE 6

The product of example 4 was used in a Chypre formulations, as follows:

| | |
|---|---|
| Musk Ambrette | 40 |
| Musk Ketone | 60 |
| Coumarin | 50 |
| Oil of Bergamot | 150 |
| Oil of Lemon | 100 |
| Methyl Ionone | 50 |
| Hexyl Cinnamic Aldehyde | 100 |
| Hydroxycitronellal | 100 |
| Oil of Lavender | 50 |
| Oil of Sandalwood | 40 |
| "Osyrol" Preparation* | 60 |
| Isoeugenol | 20 |
| Eugenol | 10 |
| Benzyl Acetate | 30 |
| Phenyl Ethyl Alcohol | 40 |
| Oakmoss absolute | 30 |
| Oil of Vetiver | 20 |
| Product of Example 4 | 50 |
| | 1.000 |

*"Osyrol" is a trademark of Bush Boake Allen Limited.

EXAMPLE 7

The products of Examples 1 and 3 were used Fougere formulation, as follows:

| | |
|---|---|
| Musk Ambrette | 100 |
| Musk Ketone | 50 |
| Coumarin | 50 |
| Oil of Lavender | 100 |
| Oil of Patchouli | 30 |
| Oil of Geranium | 40 |

| -continued | |
|---|---|
| Oil of Sandalwood | 30 |
| Oil of Bergamot | 100 |
| Linalool | 50 |
| Linalyl Acetate | 50 |
| β-methyl Ionone | 60 |
| Anisaldehyde | 30 |
| Methyl Anthranilate | 5 |
| Vanillan | 55 |
| Rose absolute synthetic | 20 |
| Jasmin absolute synthetic | 20 |
| Oil of Ylang | 10 |
| Hydroxycitronellal | 100 |
| Product of Example 3 | 50 |
| Product of Example 1 | 100 |
| | 1,000 |

EXAMPLE 8

The products of Example 1,2 and 3 were used in an After-Shave formulation as follows:

| | |
|---|---|
| Oil of Bergamot (bergaptene free) | 110 |
| Oil of Lemon | 90 |
| Oil of Petitgrain | 20 |
| Oil of Geranium | 60 |
| Oil of Lavender | 40 |
| Oil of Neroli | 10 |
| Oil of Galbanum | 10 |
| Oil of Sandalwood E.I. | 40 |
| Hexyl Cinnamic Aldehyde | 50 |
| Hydroxycitronellal | 80 |
| 1-Citronellol | 40 |
| Hedione | 20 |
| Exaltolide | 10 |
| Musk Ambrette | 50 |
| Musk Ketone | 30 |
| Coumarin | 20 |
| Isoeugenol | 10 |
| Styrallyl Acetate | |
| Oil of Angelica Root 10% in DEP | 20 |
| Aldehyde C.12 MNA 10% in DEP | 10 |
| Aldehyde C.11 Undecylenic 10% in DEP | 10 |
| Oakmoss absolute | 20 |
| Labdanum Resinoide | 10 |
| Vetiveryl Acetate | 30 |
| Product of Example 1 | 100 |
| Product of Example 2 | 50 |
| Product of Example 3 | 50 |
| | 1,000 |

We claim:

1. A compound having the formula XY, wherein X is a polycyclic monovalent radical selected from the group consisting of II, III and IV:

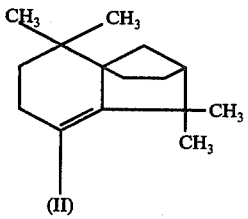
(II)

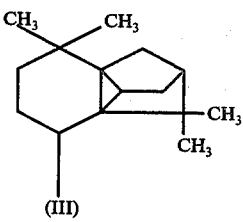
(III)

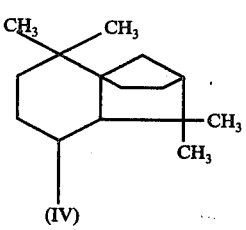
(IV)

Y is —C(OR'$_n$) (H)$_n$R, $n$ is 0 or 1, R is selected from the group consisting of hydrogen and alkyl groups having from 1 to 5 carbon atoms and R' is selected from the group consisting of hydrogen and alkanoic acid residues having from 1 to 6 carbon atoms.

2. A compound as claimed in claim 1 wherein X is a radical selected from the group consisting of II and III, $n$ is 0 and R is hydrogen.

3. A compound as claimed in claim 1 wherein X is a radical selected from the group consisting of II and III, $n$ is 0 and R is an alkyl group having from 1 to 5 carbon atoms.

4. A compound as claimed in claim 1 wherein X is a radical selected from the group consisting of II and III, $n$ is 1, R' is hydrogen and R is hydrogen.

5. A compound as claimed in claim 1 wherein X is a radical selected from the group consisting of II and III, $n$ is 1, R is hydrogen and R' is an alkanoic acid residue having from 1 to 6 carbon atoms.

6. A compound according to claim 5 wherein R' is a formyl residue.

7. A compound according to claim 5 wherein R' is an acetyl residue.

8. A compound as claimed in claim 1 wherein X is a radical selected from the group consisting of II and III, $n$ is 1, R' is hydrogen and R is an alkyl group having from 1 to 5 carbon atoms.

9. A compounded perfumery composition comprising ingredient (i) in an amount between 0.01 and 20% by weight of the compounded perfumery composition, and ingredient (ii) a plurality of odiferous ingredients in addition to said ingredient (i); said ingredient (i) being at least one compound as claimed in claim 1.

10. A compounded perfumery composition comprising ingredient (i) in an amount between 0.01 and 20% by weight of said compounded perfumery composition and being at least one compound as claimed in claim 2, and ingredient (ii) a plurality of odiferous ingredients in addition to said ingredient (i).

11. A compounded perfumery composition comprising ingredient (i) in an amount between 0.01 and 20% by weight of said compounded perfumery composition and being at least one compound as claimed in claim 3, and ingredient (ii) a plurality of odiferous ingredients in addition to said ingredient (i).

12. A compounded perfumery composition comprising ingredient (i) in an amount between 0.01 and 20% by weight of said compounded perfumery composition and being at least one compound as claimed in claim 4, and ingredient (ii) a plurality of odiferous ingredients in addition to said ingredient (i).

13. A compounded perfumery composition comprising ingredient (i) in an amount between 0.01 and 20% by weight of said compounded perfumery composition and being at least one compound as claimed in claim 5, and ingredient (ii) a plurality of odiferous ingredients in addition to said ingredient (i).

14. A compounded perfumery composition comprising ingredient (i) in an amount between 0.01 and 20% by weight of said compounded perfumery composition and being at least one compound as claimed in claim 6, and ingredient (ii) a plurality of odiferous ingredients in addition to said ingredient (i).

15. A compounded perfumery composition comprising ingredient (i) in an amount between 0.01 and 20% by weight of said compounded perfumery composition and being at least one compound as claimed in claim 7, and ingredient (ii) a plurality of odiferous ingredients in addition to said ingredient (i).

16. A compounded perfumery composition comprising ingredient (i) in an amount between 0.01 and 20% by weight of said compounded perfumery composition and being at least one compound as claimed in claim 8, and ingredient (ii) a plurality of odiferous ingredients in addition to said ingredient (i).

17. The compounded perfumery composition of claim 9 wherein said ingredient (ii) contains odiferous ingredients selected from the group consisting of 2,6-dimethyl-2-alkoxy octan-7-ol, vetivert oil, vetiverol, vetiveryl acetate, guaiac wood oil, guaiac wood acetate, coumarin musk ketone, lauric aldehyde, benzyl acetate, lemon oil, dimethyl benzyl carbinol, dimethyl benzyl carbinyl acetate, rose absolute, jasmin absolute, ionones, iso-nonyl acetate, methyl phenyl acetate, styrallyl acetate, B phenyl ethanol, citronellol, citronellal, hydroxy citronellal, geranium oil, geraniol, linalol, nerol, lavandin oil, lanalyl acetate, patchouli oil, petitgrain oil, bergamot oil, heliotropin, ethylene brassylate, undecyl aldehyde, cinnamaldehyde, benzyl salicylate, cinnamyl alcohol, clove bud oil, bay oil, nutmeg oil, pimento berry oil, terpineol, ylang oil, benzyl benzoate, sandalwood oil, clary sage oil, amyl salicylate, labdanum resin, methyl ionones, dihydromyrcenol, orange oil, vanillin, ethylvanillin, olibanum resin, musk ambrette, rhodinol, mandarin oil, methylnonyl acetaldehyde, neroli oil, cedrol, oakmoss, isovalanone, eugenol, iso-eugenol, cedarwood oil, and p-tert-butyl cyclohexyl acetate.

18. The compounded perfumery composition of claim 9 wherein said ingredient (ii) contains odiferous ingredients selected from the group consisting of cedarwood, sandalwood, vetiver, lavender, bergamot, geranium, patchouli, oakmoss, clary sage, musk ambrette, musk ketone, musk xylene, cedrol, cedryl acetate, acetyl cedrene, vetiverol, vetiveryl acetate, methyl ionone, coumarin, linalool, linalyl acetate, geraniol, citronellol, phenyl ethyl alcohol, benzyl acetate, eugenol, iso-eugenol, amyl - and hexylcinnamin aldehyde, and hydroxycitronellal.

19. A compound as claimed in claim 1 wherein X is a radical selected from the group consisting of II and III, and R' is a $C_{1-6}$ alkanoic acid residue.

20. A compound as claimed in claim 19 wherein $n$ is 1.

21. A compound as claimed in claim 1 wherein X is the radical III.

22. A compounded perfumery composition comprising ingredient (i) in an amount between 0.01 and 20% by weight of the compounded perfumery composition, and ingredient (ii) a plurality of odiferous ingredients in addition to said ingredient (i); said ingredient (i) being at least one compound as claimed in claim 21.

23. A mixture of at least two polycyclic compounds comprising
(i) a polycyclic compound XY wherein X is the radical

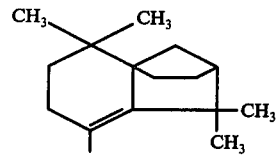

Y is $-C(OR'_n)(H)_nR$, $n$ is 0 or 1, R is selected from the group consisting of hydrogen and alkyl groups having from 1 to 5 carbon atoms and R' is selected from the group consisting of hydrogen and alkanoic acid residues having from 1 to 6 carbon atoms; and (ii) a polycyclic compound X'Y wherein X' is the radical

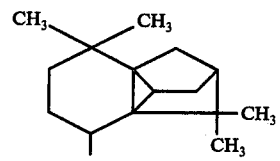

and Y is the same as in compound (i).

24. A compounded perfumery composition comprising ingredient (i) in an amount between 0.01 and 20% by weight of the compounded perfumery composition, and ingredient (ii) a plurality of odiferous ingredients in addition to said ingredient (i); said ingredient (i) being the mixture as claimed in claim 23.

* * * * *

UNITED STATES PATENT AND TRADEMARK OFFICE
CERTIFICATE OF CORRECTION

PATENT NO. : 4,100,110

DATED : July 11, 1978

INVENTOR(S) : HIFZUR RAHMAN ANSARI et al

It is certified that error appears in the above–identified patent and that said Letters Patent are hereby corrected as shown below:

Title page of patent, after "Foreign Application Priority Data", replace "25244/74" with ---35244/74---.

Signed and Sealed this

Second Day of October 1979

[SEAL]

Attest:

RUTH C. MASON
Attesting Officer

LUTRELLE F. PARKER
Acting Commissioner of Patents and Trademarks